United States Patent [19]
Doebert et al.

[11] Patent Number: 5,511,106
[45] Date of Patent: Apr. 23, 1996

[54] X-RAY DIAGNOSTICS INSTALLATION FOR PRODUCING X-RAY EXPOSURES OF BODY PARTS OF A PATIENT

[75] Inventors: Michael Doebert, Lorsch; Werner Guenther, Bensheim; Ulrich Schulze-Ganzlin, Lorsch; Joseph Ploetz, Bensheim; Erich Huebeck, Bensheim; Manfred Franetzki, Bensheim, all of Germany

[73] Assignee: Siemens Aktiengesellschaft, Munich, Germany

[21] Appl. No.: 269,058

[22] Filed: Jun. 30, 1994

[30] Foreign Application Priority Data

Jul. 6, 1993 [DE] Germany ............... 43 22 483.0
May 30, 1994 [EP] European Pat. Off. ......... 94108334
Jun. 17, 1994 [EP] European Pat. Off. ......... 94109424

[51] Int. Cl.⁶ ........................................ A61B 6/03
[52] U.S. Cl. ........................... 378/146; 378/39; 378/40
[58] Field of Search ................... 378/38, 39, 40, 378/146, 145, 147, 149, 154, 155, 204

[56] References Cited

U.S. PATENT DOCUMENTS

| | | | |
|---|---|---|---|
| 4,188,537 | 2/1980 | Franke | 378/146 X |
| 4,411,012 | 10/1983 | Pfeiler et al. | 378/146 X |
| 4,686,695 | 8/1987 | Macovski | 378/146 |
| 4,811,372 | 3/1989 | Doebert et al. | |
| 4,870,673 | 9/1989 | Adler et al. | |
| 4,878,234 | 10/1989 | Pfeiffer et al. | |
| 4,953,192 | 8/1990 | Plewes | 378/146 |
| 4,995,062 | 2/1991 | Schulze-Ganzlin et al. | 378/40 X |
| 5,018,177 | 5/1991 | McDavid et al. | 378/146 X |
| 5,023,898 | 6/1991 | Kawasaki et al. | 378/146 |
| 5,040,199 | 8/1991 | Stein | 378/146 X |
| 5,054,048 | 10/1991 | Wang | 378/146 |
| 5,058,147 | 10/1991 | Nishikawa et al. | 378/38 |
| 5,138,166 | 8/1992 | Makino et al. | 378/40 X |
| 5,195,114 | 3/1993 | Sairenji et al. | 378/39 X |
| 5,307,396 | 4/1994 | Tsuchino | 378/146 |
| 5,418,832 | 5/1995 | Barnes | 378/146 |

FOREIGN PATENT DOCUMENTS 0166567  1/1986  European Pat. Off.
54138659  5/1992  Germany.

*Primary Examiner*—David P. Porta
*Attorney, Agent, or Firm*—Hill, Steadman & Simpson

[57] ABSTRACT

An x-ray diagnostics installation for producing x-ray exposures of body parts of a patient has a line detector camera arranged diametrically opposite a radiation source, the line detector camera containing an x-ray detector arranged behind a slot-shaped opening, the width of the x-ray detector being matched to the width or length of the body part to be registered. An adjustment system adjusts the line detector camera relative to the body part such that the slot opening is moved along the body part, whereby the fan beam limited by the radiation diaphragm of the radiation source is moved synchronously relative to the camera motion. The line detector camera can be horizontally or vertically arranged.

22 Claims, 13 Drawing Sheets

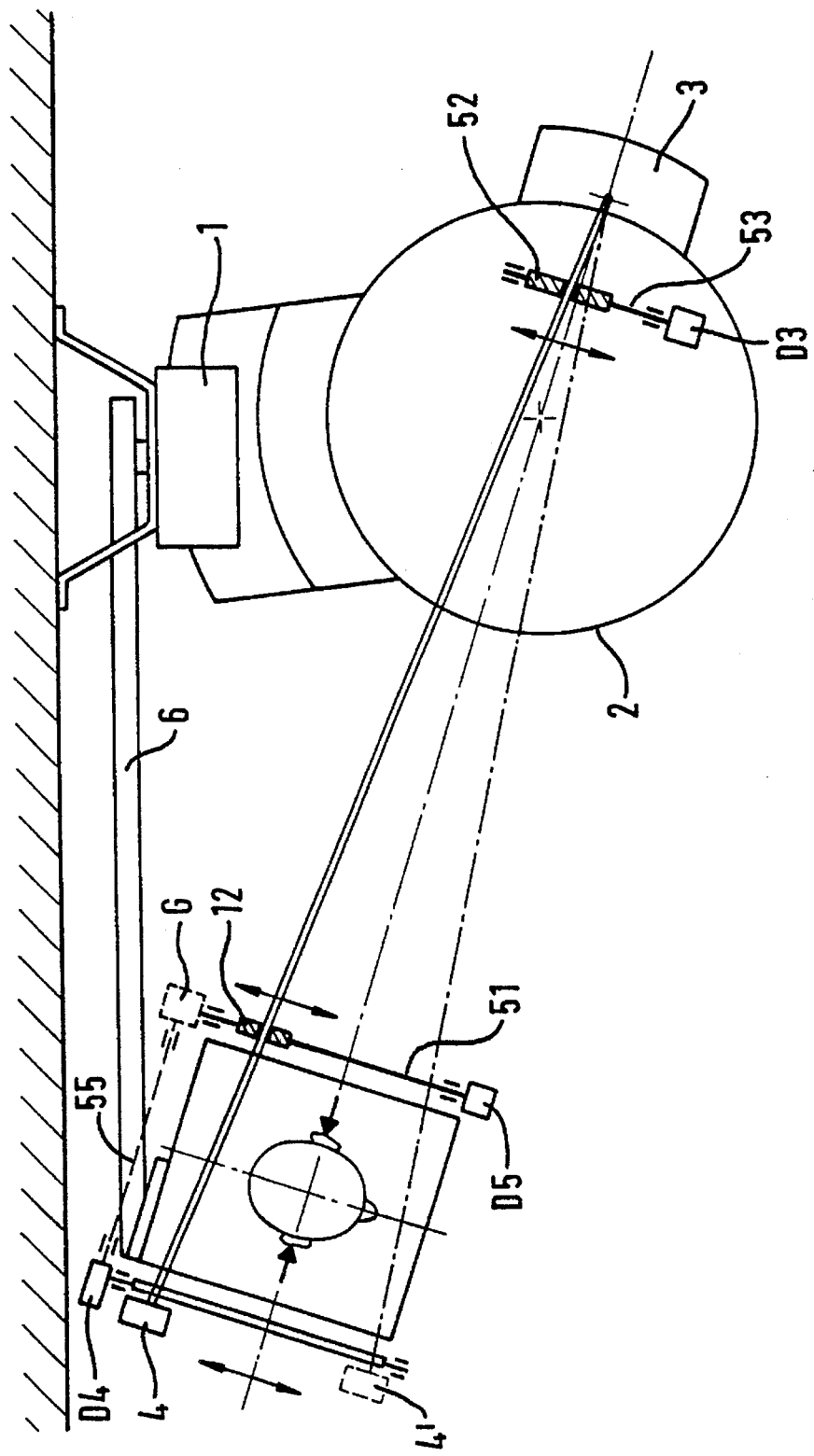

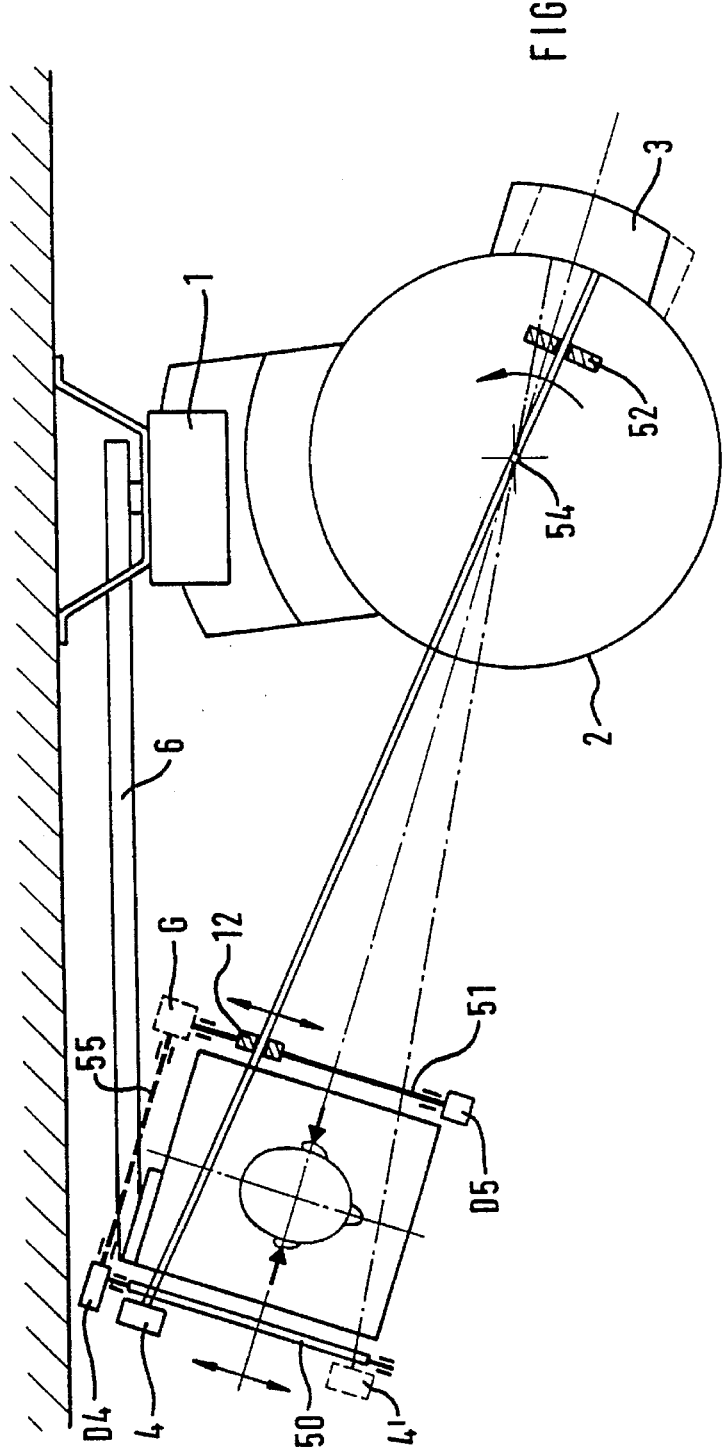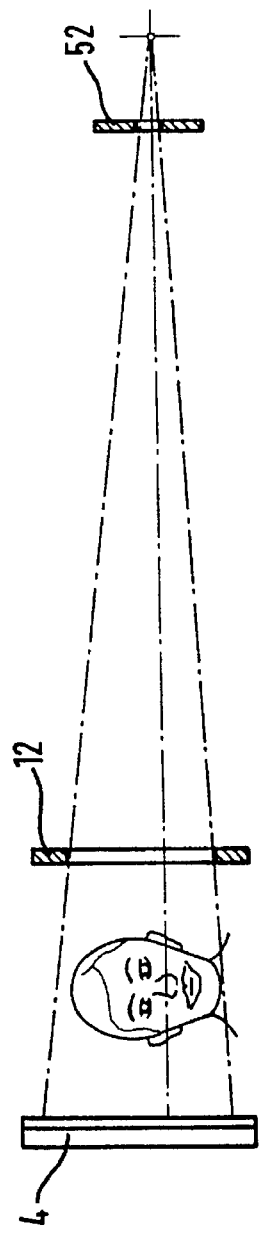

X-RAY DIAGNOSTICS INSTALLATION FOR PRODUCING X-RAY EXPOSURES OF BODY PARTS OF A PATIENT

BACKGROUND OF THE INVENTION

1. Field of the Invention

The present invention is directed to an x-ray diagnostics installation for producing x-ray exposures of body parts of a patient.

2. Description of the Prior Art

It is currently necessary and standard for producing, for example, jaw, skull or mammary exposures, to arrange a film cassette with the x-ray film to be exposed following the transirradiated body part. In order to be able to make skull (ceph) exposures, European Application 0 262 522, corresponding to U.S. Pat. No. 4,870,673 discloses the; use of a skull holder that is secured with a carrier to a boom that is in turn secured with the necessary spacing to a stand at which the x-ray radiator is also arranged. A holder for accepting the x-ray film cassette in the size necessary for ceph exposures is situated at the skull holder.

A different film cassette having a different film format is to be provided for so-called panorama x-ray exposures (PAN exposures), this film cassette being adjusted synchronously but oppositely relative to the motion of the radiation source. In a known device of this type (European Application 0 229 308, corresponding to U.S. Pat. No. 4,811,372), a rotary unit arranged at a carriage of a stand is provided, the radiation source and a holder for a film cassette accepting the x-ray film being arranged at said rotatory unit diametrically opposite each other. In order to also be able to make ceph exposures with this x-ray diagnostics installation, the aforementioned boom is adjusted relative to the carriage of the stand, the head-holder and positioning means as well as the holder for the film cassette suitable for ceph exposures being secured to this boom.

SUMMARY OF THE INVENTION

An object of the, present invention is to provide an x-ray diagnostics installation which makes the above types of exposures without film and film cassette, but instead by acquiring sensor data with economically justifiable outlay.

The above object is achieved in accordance with the principles of the present invention in an x-ray diagnostics installation for producing x-ray exposures of body parts of a patient having a line detector camera disposed diametrically opposite a radiation source, the line detector camera containing an x-ray detector arranged behind a slotshaped opening. The width of the x-ray detector is matched to the width or length (depending on the orientation of the arrangement for a particular type of imaging) of the body part to be registered. An adjustment arrangement is provided which adjusts the line detector camera relative to the body part so that the slot opening is moved along the body part while the body part is being irradiated by a fan beam from the radiation source. The fan beam, limited by a radiation diaphragm, is moved synchronously with the camera motion.

The employment of a line detector makes it possible to produce PAN as well as ceph or mammary exposures in slot technique. The line detector can be horizontally arranged or upright. It advantageously contains a plug connection that can be connected as needed to a suitable plug-in location of a PAN, ceph or mammary apparatus. The x-ray dose that is applied is defined by the thickness of the ray fan and by the displacement speed thereof. In ceph exposures, for example, the head of the standing or seated patient is swept from top to bottom with a laterally open ray fan that always exactly impinges the horizontally arranged sensor and covers the length and width thereof. Given a vertical arrangement, the radiation source can be pivoted in horizontal direction or can be translationally moved with a motor drive; alternatively, the secondary diaphragm can be pivoted or moved translationally synchronously relative to the line detector given a stationary radiation source.

Particular advantages given employment in the dental field are that the same line detector can be employed for both PAN or ceph exposures, this line detector being preferably held vertically in the one exposure type and preferably held horizontally in the other. The manufacturing outlay for the overall apparatus can thus be considerably reduced.

A further object of the invention is to provide a dental x-ray diagnostics installation with which it is possible to produce tomosynthetic exposures with comparatively little outlay. In tomosynthesis, a subject is transirradiated from various projection directions and the resulting two-dimensional images are subsequently processed in a computer to form tomograms and three-dimensional images. The registration of the images can ensue on film material in a conventional way or can ensue via electronic image converters (x-ray image intensifiers, CCD cameras or digital cameras on the basis of amorphous silicon). The invention is based on the perception of utilizing the essential components of apparatus known in orthopanthomography and cephalometry and modifying these components with suitable auxiliary components such that the aforementioned exposures can be produced with little outlay. A further object is to modify a panorama x-ray apparatus for the purpose of producing remote x-ray images of the skull in a conventional way, i.e. graphic identification of the aggregate absorption given complete transirradiation of the skull employing tomosynthetic calculating methods.

DESCRIPTION OF THE DRAWINGS

FIGS. 8 and 9 are respective schematic illustrations of further embodiments of an x-ray diagnostics apparatus of the invention for producing ceph exposures.

FIG. 10 is a schematic illustration of the beam path in the apparatus of the invention.

DESCRIPTION OF THE PREFERRED EMBODIMENTS

Figure 1:
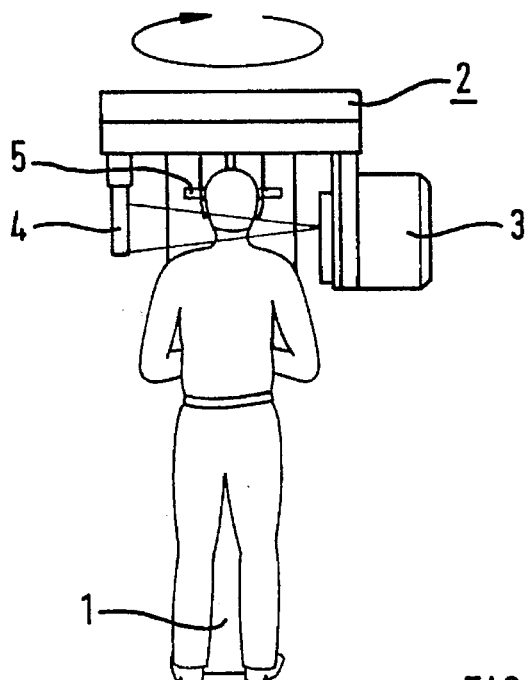
FIG. 1 is a schematic illustration of a dental x-ray diagnostics apparatus for producing PAN exposures constructed in accordance with the principles of the present invention.

FIG. 1 shows a schematic illustration of a dental x-ray diagnostics apparatus for producing panorama tomograms, referred to below abbreviated as PAN exposures. The apparatus contains a height-adjustable carrying column 1 at which a rotatory unit 2 is held, forming a carrier for an x-ray source 3 and an x-ray line camera 4 diametrically relative thereto.

The installation also has a (first) head-holder 5 and positioning means with which the patient's head can be fixed in a defined position in a known way. The structure as well as adjustment possibilities of the rotatory unit and of the head-holder and positioning means are known and are disclosed, for example, in European Application 0 229 308.

Figure 2:
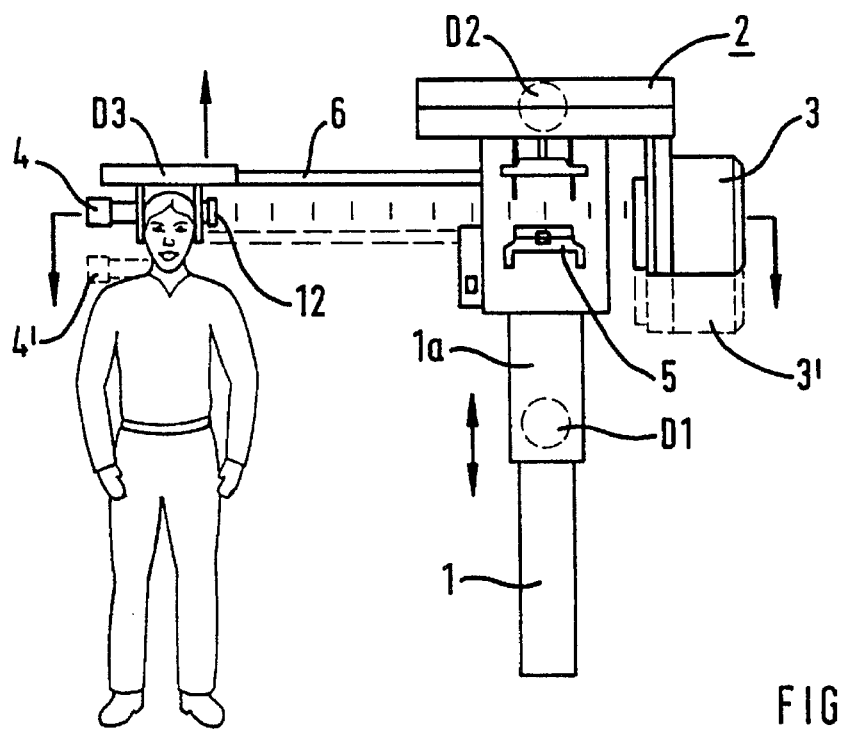
FIG. 2 shows the apparatus of FIG. 1 modified for producing ceph exposures.

FIG. 2 shows the same basic apparatus composed of height-adjustable carrying column 1, rotatory unit 2 and x-ray radiator 3, but supplemented by a device adaptable at the apparatus with which remote skull exposures, referred to below abbreviated as ceph exposures, can be produced. Before this apparatus is set forth in greater detail, it should be mentioned that the carrying column 1 is height-adjustable with a drive D1 in the indicated arrow direction, and that the rotatory unit 2 can be turned and pivoted with one or more drives D2 in order to be able to make a PAN exposure. Details with respect thereto are disclosed in the aforementioned European Application 0 229 308.

Figure 3:
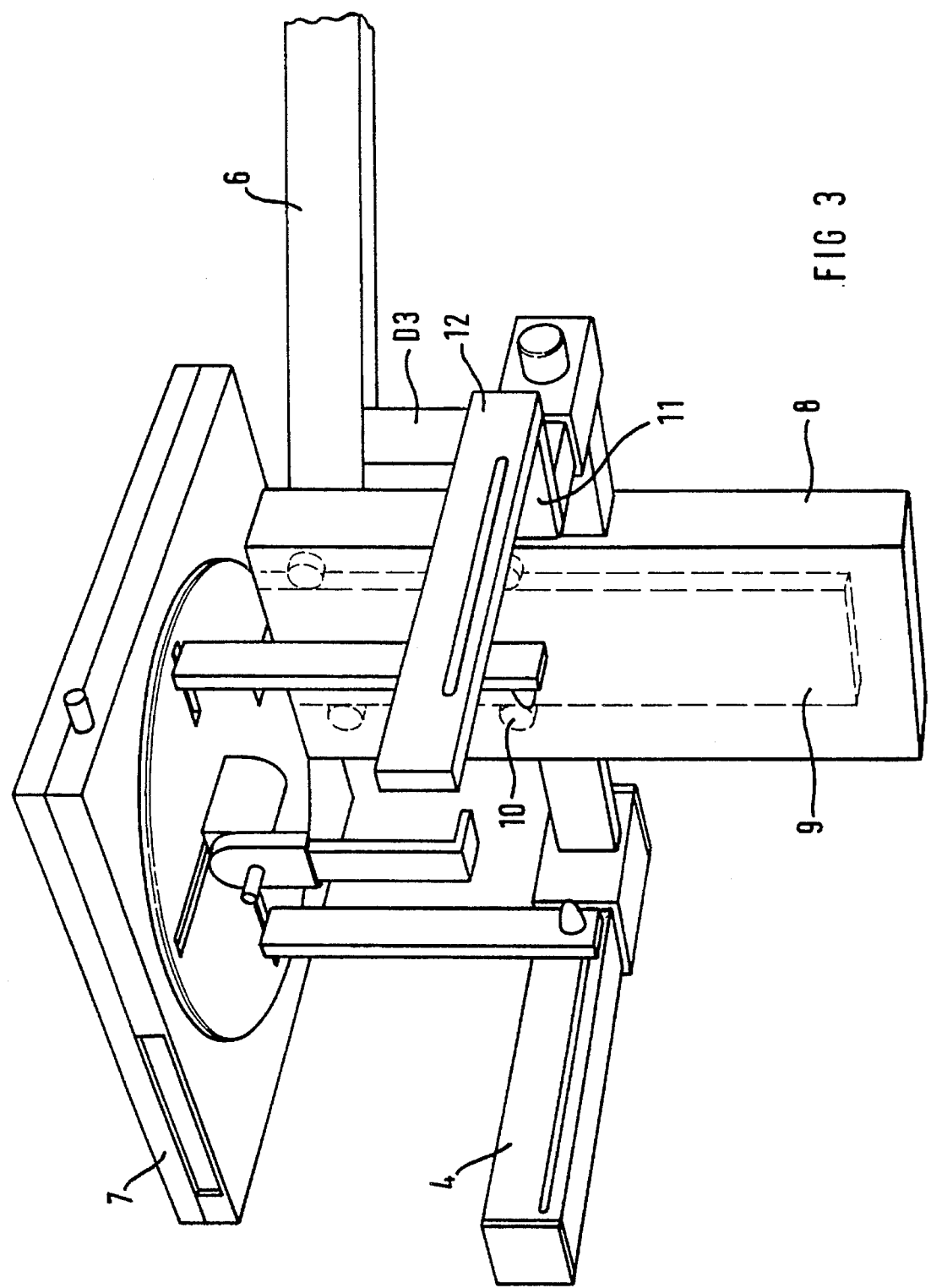
FIG. 3 is a schematic illustration of the apparatus provided for ceph exposures.

FIG. 3 shows a schematic illustration of the aforementioned device for producing ceph exposures.

A boom 6 that carries a (second) head-holder 7 and positioning means is secured to the height-adjustable part 1a of the carrying column 1 (FIG. 2). The boom 6 has a housing 8 at which a blade 9 that carries the head-holder 7 and positioning means is adjustably seated by guide rollers 10 arranged in the housing 8. The line camera 4 is connected by a traverse element 11 to a pre-diaphragm 12 that serves the purpose of again exactly adjusting the fan beam (already limited in a known way by the secondary diaphragm neighboring the x-ray source 3) onto the slot width and length of the line camera, to be set forth in greater detail below.

By contrast to the exemplary embodiment of FIG. 1, the line camera in the embodiment of FIG. 2 is not vertically arranged but is horizontally arranged. A correspondingly fashioned holder is shown in FIG. 5.

Figure 4:
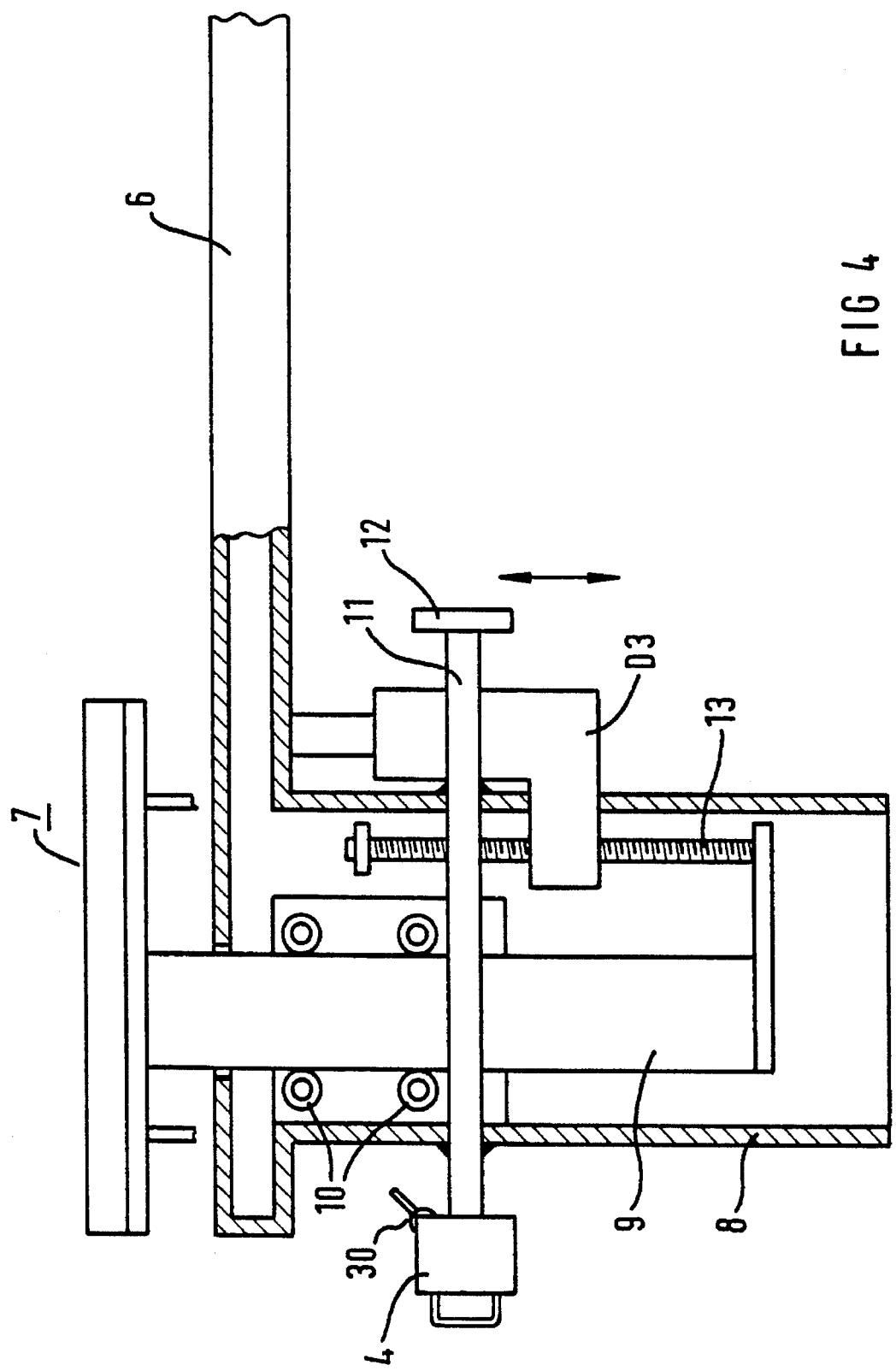
FIG. 4 shows the apparatus of FIG. 3 in a front view, partially in section.

As may be seen from FIG. 4, which shows the apparatus in a front view and partially in section, a threaded spindle 13 that cooperates with a geared motor generally referenced D3 is located at the blade 9 that carries the head-holder 7 and positioning means. The geared motor D3 is secured either to the housing 8 or to the boom 6. As shall be set forth in greater detail below, what is achieved with the assistance of the illustrated adjustment arrangement having the drive D3 permits the head-holder 7 and positioning means to effectively execute no motion during the ceph exposure, i.e., it is held stationarily in space, when the x-source 3 together with the line camera 4 are vertically moved.

Figure 5:
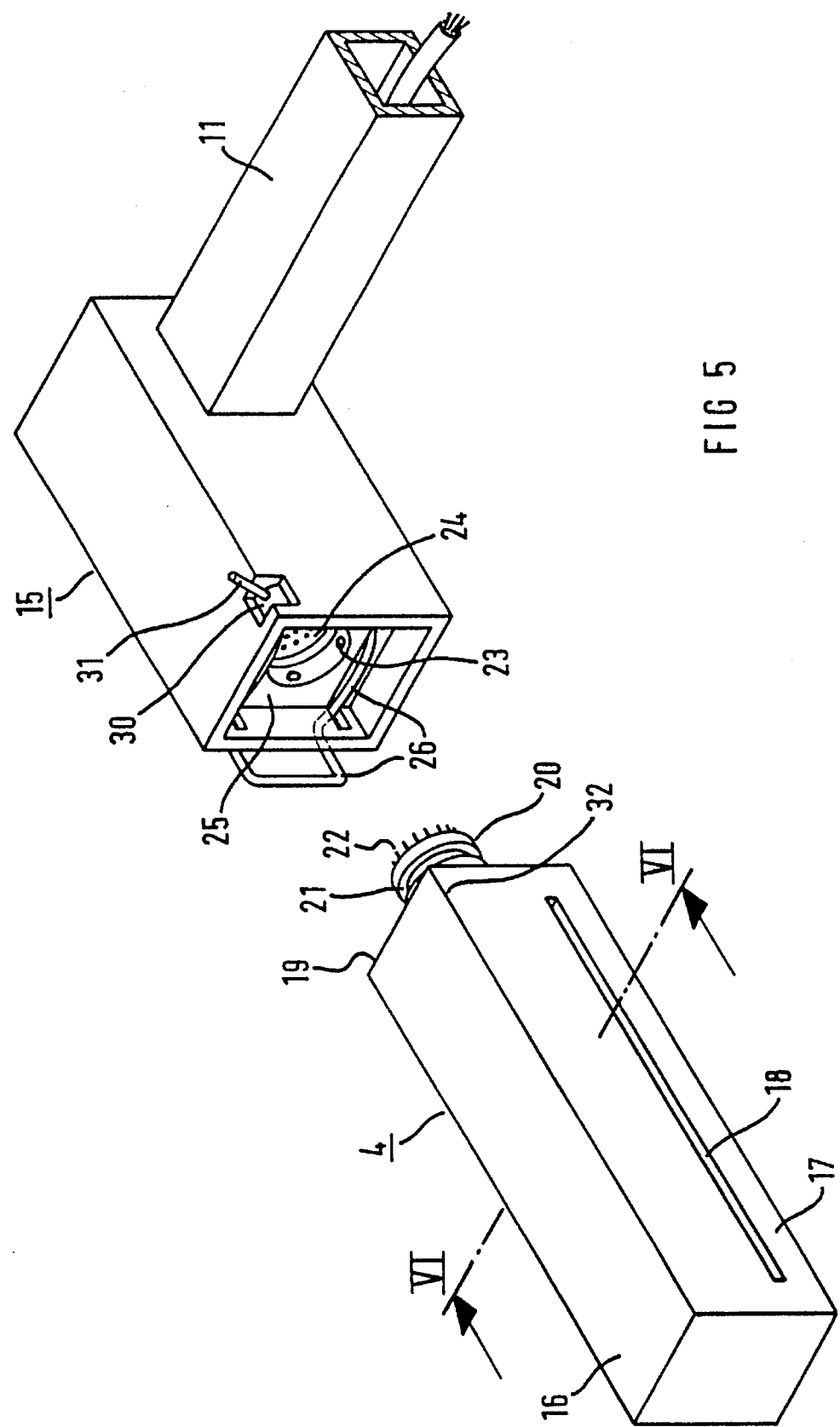
FIG. 5 is an embodiment of a line detector camera and its holder constructed in accordance with the principles of the present invention, in a schematic, exploded view.

FIG. 5 shows a schematic, exploded view of, first, the line camera 4 and, second, a holder 15 that is secured to the traverse element 11 for the embodiment of FIG. 2. In the case of the version of FIG. 1 (for PAN exposures), an identically fashioned holder (but without the traverse element 11) is vertically secured to the rotatory unit 2 (FIG. 1).

The line camera 4 contains an oblong housing 16 that is composed of a rectangular tube in the exemplary embodiment and that has a slot 18 in the front lateral surface 17 facing toward the radiation source 3. The slot 18 is located in the lower third of the lateral surface 17, as a result of which the line camera can be moved into a comparatively low initial position (see the broken-line illustration in FIG. 2).

Figure 6:
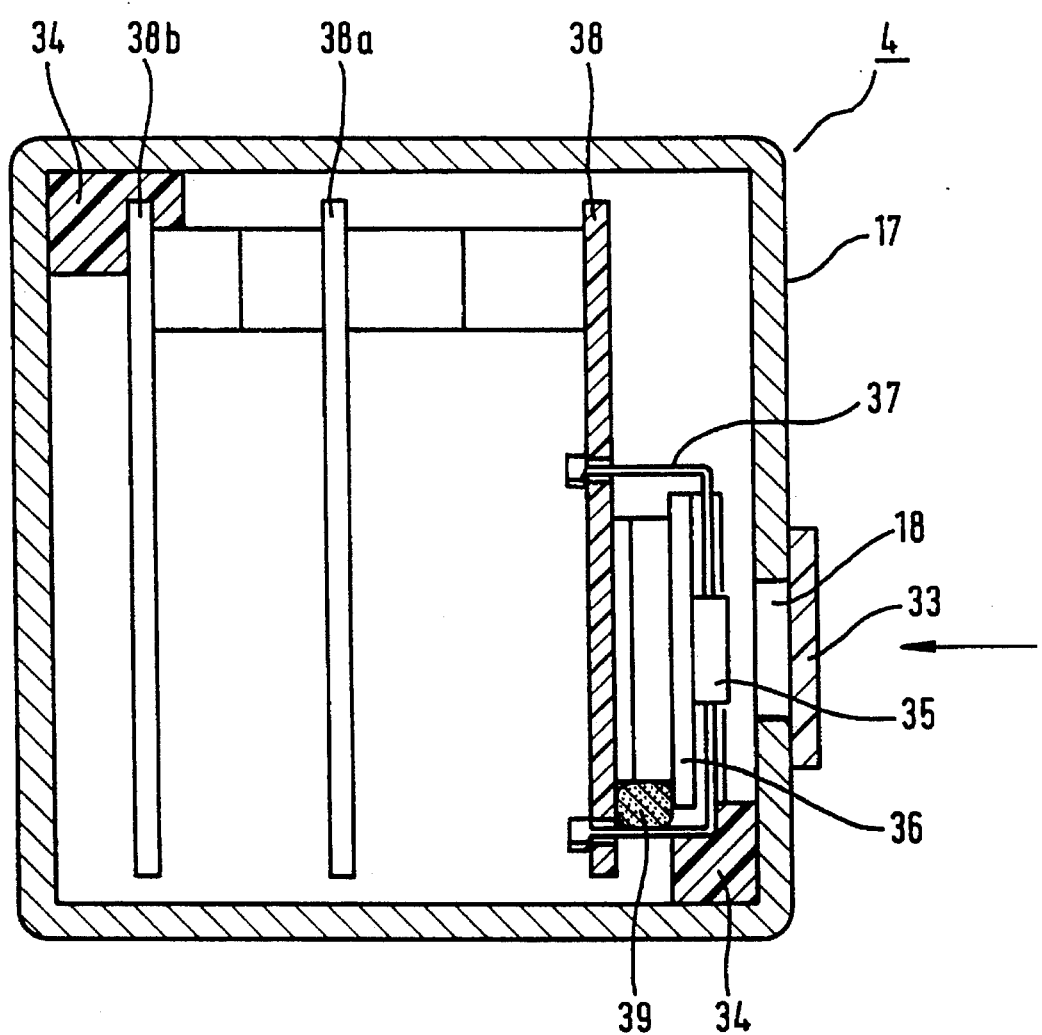
FIG. 6 shows the line detector camera in cross-section along the line VI—VI of FIG. 5.

As proceeds in further detail from FIG. 6, a radiation-sensitive line detector in the form, for example, of a CCD sensor is located behind the slot 18 in the inside of the profiled tube 16. A peg-shaped connector element 20 that forming mechanical and electrical connector means to the holder 15 is located at the one face side 19. The mechanical connector means include an annular channel 21 that cooperates with a ball catch 23. The electrical connector means are composed of a multi-pin plug 22 that interacts with a socket 24 in the holder 15. The pins of the plug 22 are connected to the aforementioned line detector and to further electronics located in the inside of the line camera 4. The holder 15 is constructed such that the face side 19 of the line camera 4 resides opposite an end face connecting surface 25 of the holder 15 when the line detector is put in place.

An ejector mechanism 26 is provided so that the release of the line camera 4 from the holder 15 is facilitated, particularly to prevent tilting, and thus the risk of damage to the highly sensitive electrical contacts. This ejector mechanism 26 in the present embodiment is composed of a shackle that is conducted to the outside in a slot of the housing wall of the holder 15. When the shackle is actuated with the line camera in place, adjacent shackle parts press against the end face 19 and thus exert a central force on the surface, as a result of which the connection can be easily released.

A centering mechanism 30 that includes a lever 31 is eccentrically seated in the housing of the holder. After the introduction of the line camera 4 into the holder 15, the lever 31 is actuated, as a result of which a surface of the eccentrically seated mechanism 30 presses against an edge 32 of the housing and holds said housing in a defined, reproducible position. Even though the housing is fashioned of one part in the present exemplary embodiment, the housing can alternatively be formed by multiple parts, whereby the housing part that carries the detector is then centered in the aforementioned way. The detector can thus be fixed with reference to the holder independently of the camera housing and the possible mounting and fabricating tolerances thereof.

The fundamental structure of the line camera proceeds from FIG. 6, which shows a section along the line VI, VI in FIG. 5. The housing is fashioned light-tight; the slot 18 has its end face covered by a light-opaque but x-ray-transmissive plastic plate 33. A CCD sensor 35 provided with a preceding scintillation layer, and possibly, with intervening fiber optics, is located in the inside behind this plastic plate 33. The CCD sensor 35 can be fashioned of one piece or can be multi-part and can be advantageously fashioned as a sensor matrix of amorphous silicon. A metallic holder 37 connects the carrier 36 and the CCD element 35 to a circuit board 38. Flexible contact strips 39, for example of silicone provided with gold fibers, effect the electrical contact between the sensor 35 and the circuit board 38. The circuit board 38 contains all components directly required for the drive of the CCD sensor 35. As warranted, further circuit boards 38a and 38b can be arranged in the housing. The lines departing from the circuit board or boards 38, or 38a and 38b lead to the aforementioned pins of the plug 22 (FIG. 5). Shock-absorbing elements 34 bear the detector 35 and the control boards 38, 38a and 38b in a "floating" manner in the housing. The highly sensitive and expensive parts can thus be largely protected against breakage or release of the contact connections given an unintentional dropping of the camera. As initially mentioned, the same basic apparatus and the same camera can be employed for PAN exposures (FIG. 1) and for ceph exposures (FIG. 2). In order to achieve the image size needed for a ceph exposure, the line camera advantageously has a correspondingly longer sensor. The line camera can thus be attached either to the ceph or to the PAN holder as needed. Various possibilities for holding the line camera at the holder 15 are conceivable. Instead of the illustrated ball catch, a bayonet-type connection can also be provided. Likewise, some other external shape instead of a rectangular profile can be provided for the housing of the line camera.

The following should be noted regarding the exposure principle. A PAN tomogram is achieved in such a way that the signals acquired when sweeping the subject (jaw) to be registered are added up in the two-dimensionally resolving detector; the adding of the signals—if a CCD sensor is employed—can already be implemented within the sensor by operating in that the sensor in the TDI mode. The function of a moving film is simulated by this special operating mode, in that the charge packets generated by exposure are corresponding clocked in the CCD element, whereas new charges are continuously added thereto. The clock pulses for the TDI mode are derived from the stepping motor pulses which would otherwise be required for the film cassette drive.

Alternatively, an accumulation in a later signal processing stage is possible.

Figure 7:
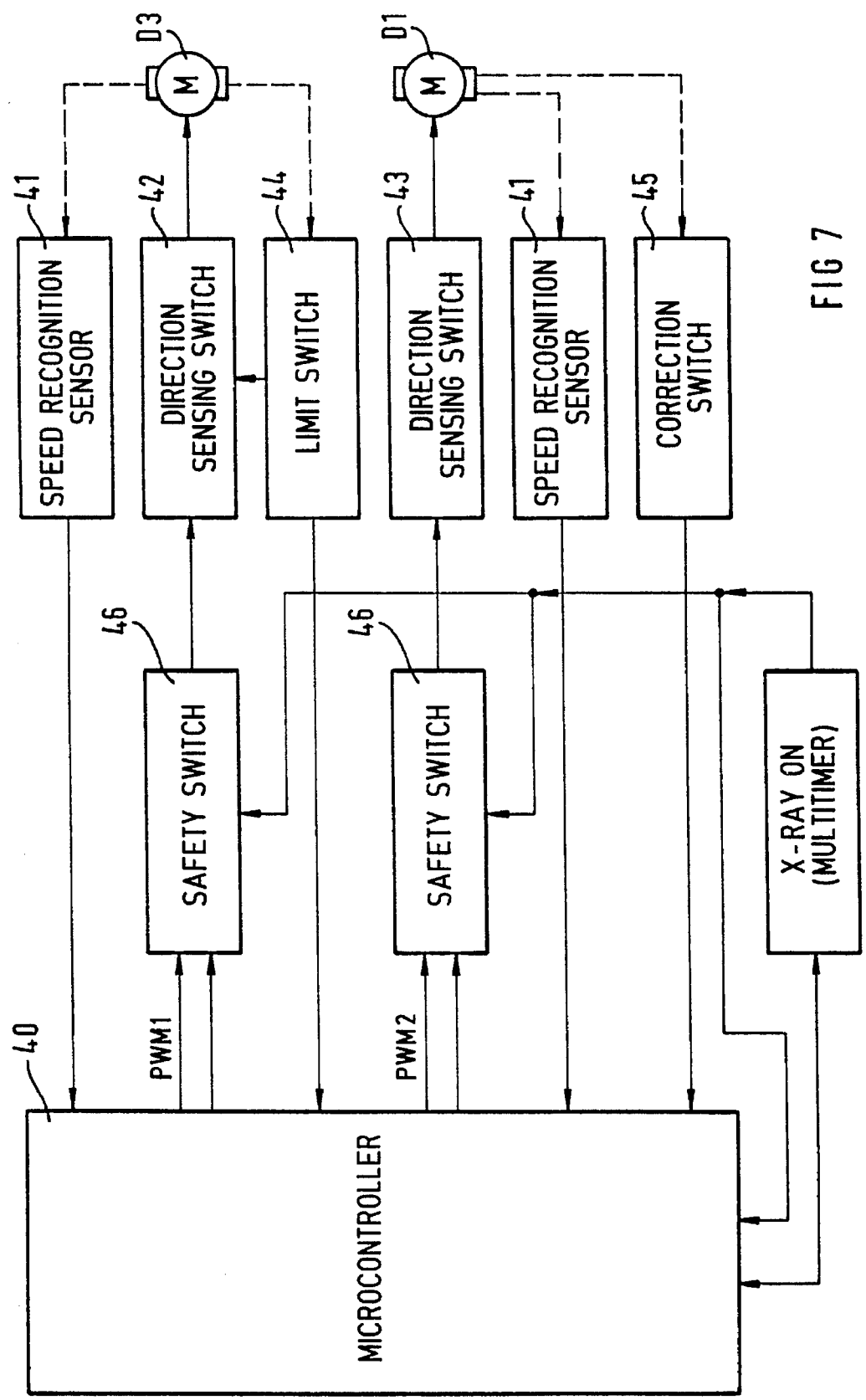
FIG. 7 shows a block circuit diagram for driving the adjusting motors in the above embodiments.

The ceph exposure is likewise carried out in slot technique. The head of a standing (or seated) patient is swept from top to bottom (given a horizontal arrangement), or from left to right (given a vertical arrangement) and vice versa, with a ray fan dependent on the arrangement of the line camera. Adjusted by the aforementioned pre-diaphragm 11, this ray fan exactly impinges the horizontally arranged slot of CCD sensor. With the assistance of the drive D1, the overall apparatus, i.e. the x-ray source 3 with primary and secondary diaphragms as well as line camera 4 with sensor, is then displaced vertically proceeding from an initial position (see the arrows in FIG. 2). Simultaneously, the head-holder 7 and positioning means is moved in the opposite direction with the assistance of the drive D3, whereby the two motions are matched such to one another so that the patient's head remains spatially fixed, i.e. stationary. The control of the two drive, motors D1 and D3 ensues via a microprocessor 40 according to the block circuit diagram of FIG. 7. Speed recognition sensors 41, direction sensing switches 42 and 43, as well as a limit switch 44 and a correction switch 45 are respectively allocated to the two drives. The control, which ensues via pulse-width modulation, also contains safety switches 46. Evaluation electronics of the microcontroller 40 recognizes which holder (PAN or ceph device) to which the camera is secured. When a ceph exposure is selected, the drive motor D3 moves into the initial position, for example, into the lower adjustment position (broken-line position in FIG. 2). The limit switch 44 responds in this position. The head-holder positioning means can now be set to the size of the patient by height adjustment of the carrying column 1. During the ceph exposure, the drive motor D3 moves the head holder 7 upwardly, whereas the drive motor D1 for the carrying column simultaneously moves downwardly. The two drives are thereby controlled such that the difference between the adjustment speeds is equal to zero. It is thus assured that the distance of the ear button, and thus of the head position from the floor remains constant. The exposure is ended when the limit switch 44 or a system clock counter (TDI clock-counter) recognizes the upper limit position.

For example, the TDI clock for the CCD sensor 36 is derived from the drive motor D1 that is provided for the height adjustment of the carrying column. Alternatively, it can also be acquired from the signals of a position that directly measures the adjustment of the carrying column. Differing from a PAN exposure, the TDI mode herein does not serve the purpose of producing a blurring and, thus, a tomogram, but serves the purpose of utilizing the full width of the sensor for the creation of the image. Here, thus, the TDI mode produces an exposure corresponding to that which would be obtained if a film were moved relative to the slot.

The following Figures show advantageous modifications of the embodiment shown in FIG. 2 on the basis of a view from above (plan view). By contrast to the embodiment of FIG. 2 wherein the line camera 4 is horizontally arranged, the line camera is vertically arranged in the versions of FIGS. 8 and 9; consequently, a vertical fan ray beam is directed onto the CCD sensor 35 by the primary diaphragm and by the pre-diaphragm.

In the embodiment of FIG. 8, the line camera 4 as well as the pre-diaphragm 12 are guided in longitudinal guides 50 and 51 that are moved by motor-drive, for example, by a common drive D4 or by separate drives D4 and D5 with a step-down gearing G. The primary diaphragm 52 can likewise be moved in the arrow direction with a longitudinal guide 53. A drive D6 is provided for this adjustment. The longitudinal guides 50 and 51 and 53 can be fashioned in a known way as motor-driven threaded spindle drives. The angular speeds for the drives D4, D5 and D6 are identical when respective separate drives are provided. When a common drive is to be provided for the longitudinal guides 50 and 51, the; two longitudinal guides must be coupled to one another via a further spindle 55 with a suitable step-down gearing G.

The carrying column is mounted by a bracket 56 to a wall 57 of the examination room.

The primary diaphragm is not moved in the embodiment of FIG. 9. On the contrary, it rotates rigidly with the rotatory unit 2 around the rotational center 54 thereof. It is also conceivable in this version to synchronize the two longitudinal guides 50 and 51 with one another with a further spindle and a suitable, intervening step-down gearing G.

FIG. 10 shows a possible embodiment of a beam alignment, namely, an asymmetric setting of the beam with reference to the subject to be transirradiated. A symmetrical alignment of the fan beam is also possible instead of the asymmetric setting.

Figure 11:
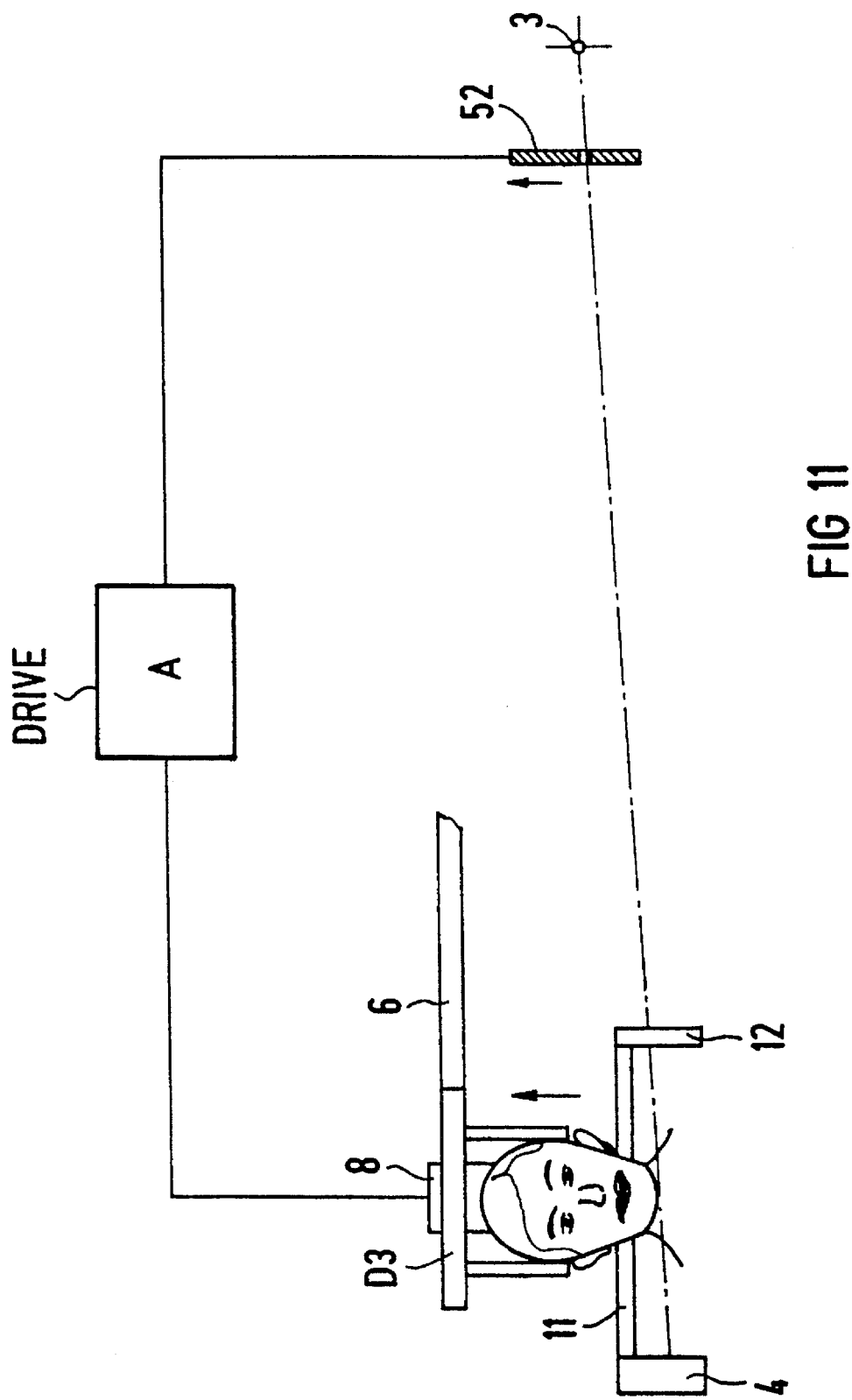
FIG. 11 is a further, advantageous embodiment of an x-ray diagnostics installation constructed in accordance with the principles of the present invention.

FIG. 11 shows a further advantageous embodiment, whereby the camera 4, as shown in FIG. 2, is horizontally arranged and is connected to the pre-diaphragm 12 via a traverse 11. The camera 4 and the pre-diaphragm 12 are motor-adjusted in common with the primary diaphragm 52 via a drive A, whereby the adjustment ensues in the TDI mode, as set forth. The radiation source 3 remains stationary in this embodiment during the adjustment motion of camera and primary diaphragm.

As proceeds from a comparison of the apparatus as disclosed in the earlier cited European Application 0 229

308 (corresponding to U.S. Pat. No. 4,811,372) to the embodiments of the above-described FIGS. 1–11, the film cassette in the known device has been replaced in accordance with the invention by an electronic radiation converter (two-dimensional line detector) in comparison to the conventional apparatus which employs x-ray film and intensifying foils. The relatively narrow sensor utilized in conventional systems receives a horizontal fan beam emitted by the x-ray radiator, whereby the arrangement of a radiator and line detector of the invention operated such that it is moved vertically past the subject on the basis of, for example, a height adjustment of the apparatus stand. The fan beam is thereby first roughly limited by the radiator-proximate primary diaphragm and is subsequently sharply limited by a subject or pre-diaphragm that is placed immediately in front of the subject and is co-moved in the vertical motion.

For tomosynthesis, the subject—the skull to be examined in the exemplary embodiment—must be; transirradiated from at least two, but preferably from even more, angular directions, whereby the projections should not lie in one plane but in different planes in order to achieve an optimum smearing. As shown below with reference to the various embodiments, it is practical to vary the projection direction upwardly, downwardly, left and right.

Figure 12:
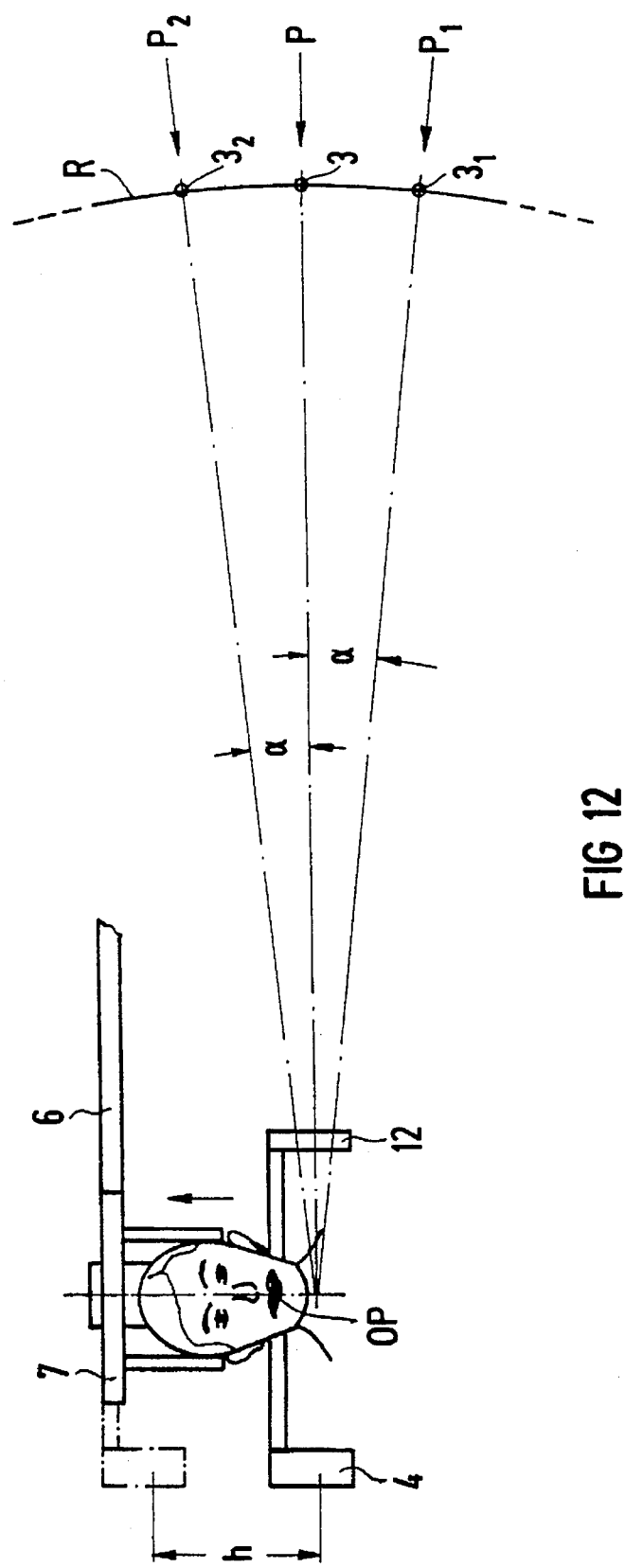
FIGS. 12–17 respective show modifications of the embodiments of FIGS. 1–11 for producing tomosynthetic e\x-ray exposures.
Figure 13:
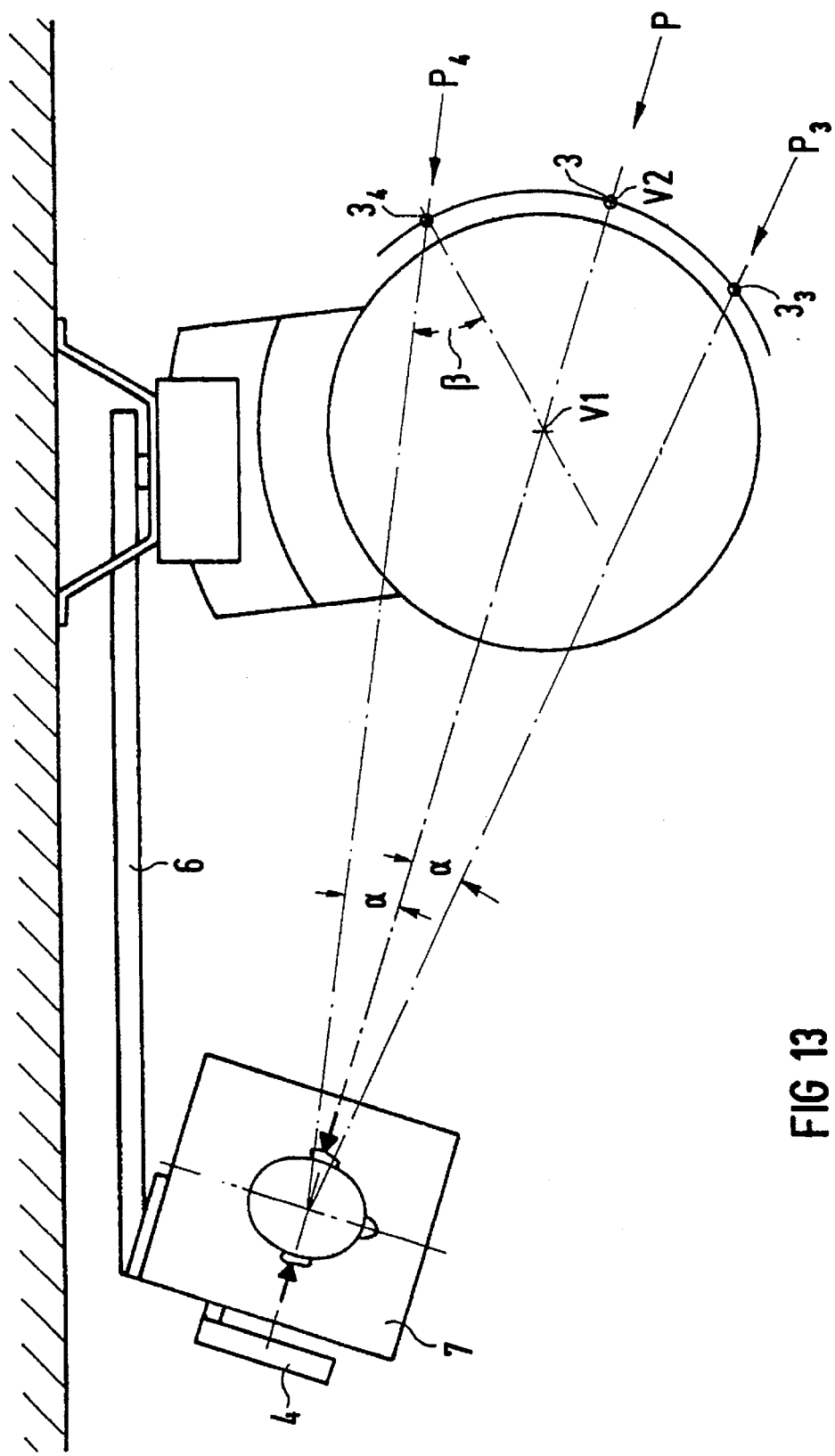

Based on the embodiment of FIG. 2, FIGS. 12 and 13 show a first modification wherein, as described above, the radiation source 3 and the line detector camera together with the pre-diaphragm 12 are not only arranged so as to be adjustable in height, i.e. in the vertical direction by the dimension h but additionally the radiator 3 (which is only schematically indicated) is laterally and vertically displaced proceeding from a fixed, horizontal projection direction P. According to FIG. 12, the radiator is pivoted around a horizontal axis on a prescribed circular path having the radius R that corresponds to the distance between radiator focus and the center of the patient's skull. The pivoting ensues by a defined angular dimension $\alpha$ that can lie roughly between 5 and 15°. A subject point (OP) of the subject (skull) to be transirradiated is thus transirradiated not only from the one projection direction P but is also transirradiated from further projection directions ($P_1$, $P_2$, $P_3$, $P_4$...) that lie in different planes, whereby the ray fan is respectively directed onto the subject with the line detector camera 4 disposed behind the subject. The subject diaphragm 12 can advantageously be correspondingly linearly displaced. Even though the line detector can remain in its position, it can be advantageous to co-rotate subject diaphragm and radiation detector. As a result, one obtains a clean blanking at the diaphragm edges and an optimum radiation detection.

As can be seen from FIG. 13, which shows the lateral displacement of the radiator 3 (likewise only schematically indicated), the radiator 3, when pivoted from the position P toward $P_3$ or $P_4$, is also turned around a radiator-proximate, vertical axis V2. The rotational angle $\beta$ is dimensioned such that a vertical transirradiation of the subject is always established in the projection directions $P_3$ and $P_4$.

As a modification of this embodiment set forth here, a large-area camera having a sensor on the basis of amorphous silicon can be employed instead of the scanning with the line detector camera 4 in the above-described slot technique with strip-by-strip formatting of the area image. The strip-by-strip scanning, i.e. the entire height adjustment of radiator, subject diaphragm and detector, could be omitted for producing a two-dimensional image.

Figure 14:
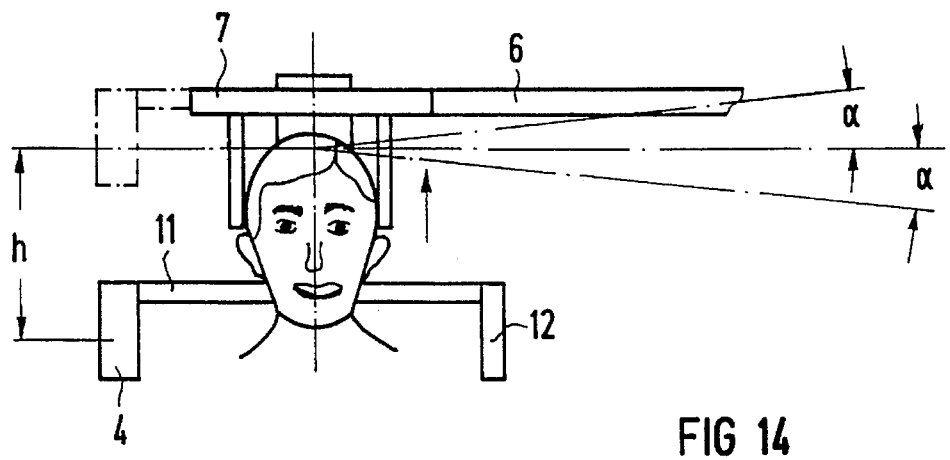
Figure 15:
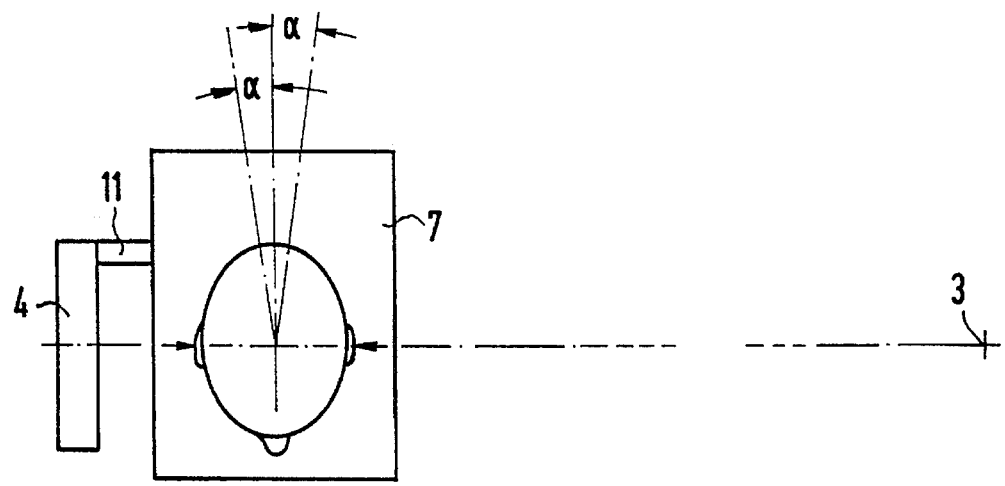

FIGS. 14 and 15 show a further embodiment. By contrast to the exemplary embodiment set forth above, the radiation source 3 is not adjusted further, with the exception of the height adjustment for scanning the skull. The radiator, diaphragms and line detector thus remain fixed relative to one another in this case, whereas the subject is mechanically coupled to the subject for producing the tomosynthetic exposures. To this end, the entire head holder 7 can be advantageously tilted up and down by the angular amount $\alpha$ relative to the carrying rod 6. The radiator, diaphragms and sensor remain fixed relative to one another, whereas the subject, the patient's head, is tilted with the head holder 7 between the individual exposures. Given this adjustment possibility, the adjustment possibilities for the ear button and the nose support that are already present can also be employed.

Figure 16:
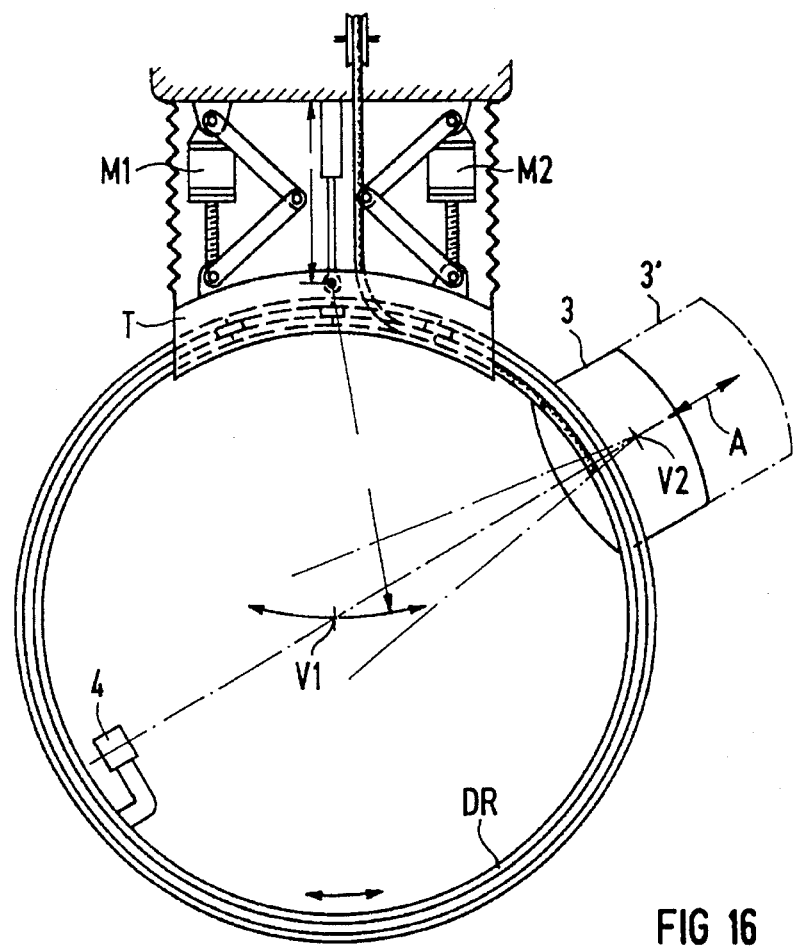
Figure 17:
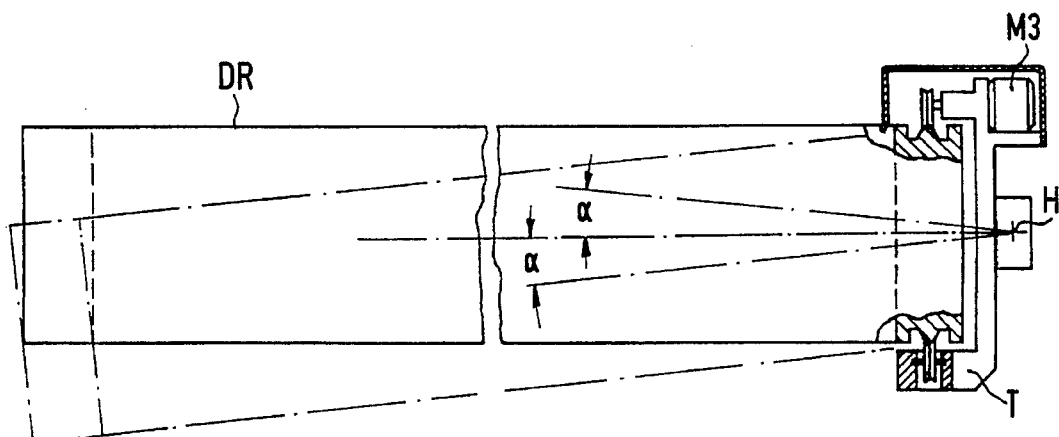

The modifications according to FIGS. 16 and 17 are based on the apparatus as disclosed in European Application 0 229 308, corresponding to U.S. Pat. No. 4,811,372 cited earlier. A line detector camera 4 is advantageously provided instead of the film cassette and, as shown in FIG. 1, is vertically arranged. The exposures for a tomosynthesis in slot technique ensue by linear, horizontal displacement of the arrangement of radiator 3 and sensor 4 relative to the subject, with the sensor 4 and the radiator 3 being moved in the same direction by respective actuators at the live ring (DR), or by displacing the live ring overall relative to the subject. It can also be advantageous, given a radiator fixed to the live ring, to pivot the sensor, for example, at the ring along the tube focus as pivot point. It is also conceivable to linearly adjust the sensor whereby either only the (radiator-proximate) primary diaphragm is correspondingly co-moved, or the diaphragm and radiator are co-rotated.

Different tomosynthetic projection angles in the horizontal direction can be set by turning the ring around the subject, with the same mechanisms as required for panorama exposures. The various projection angles in the vertical direction can be achieved by wobbling the ring around a horizontal axis H (FIG. 17), whereby the sensor is co-moved given this wobbling or tilting motion.

The head of the patient would only be covered partially in height given the geometrical conditions (spacings, angles) of the standard arrangement for panorama exposures. When, as necessary given ceph exposures, the skull is to be fully covered, complete coverage can be achieved, for example, by successively produced, height-offset images that are subsequently combined in the computer with exact relative registration. It is also conceivable to employ a specific x-ray tube that emits a beam having a larger useable angle in combination with a correspondingly longer or larger sensor. It is especially advantageous to radially adjust the radiator at the ring for these exposures and to thus bring it into a larger distance from the subject (position 3). This adjustment possibility is indicated in FIG. 16 by a double arrow at the radiator 3.

A further variation on this exemplary embodiment would be to arrange the sensor for the tomosynthesis not vertically but horizontally. The sensor can be correspondingly repositioned for PAN or for ceph exposures.

Given the solutions of FIGS. 12–15, which serve the purpose of being able to make ceph exposures, i.e. exposures of the entire skull of a patient, the skull and the xray sensor are located remote from the panorama apparatus that contains the radiator. The reason for this is to keep distortion due to the central projection low. When the boom is shortened, the distortions correspondingly increase, i.e. the radiator-proximate half of the jaw is shown larger than the radiator-distal half of the jaw given a lateral exposure of the skull.

An extreme position arises when the boom is entirely foregone and the x-ray sensor is arranged at the location that is standard in the panorama exposure (FIG. 1).

Skull exposures can be produced and tomosynthetically edited with such an arrangement in conformity with the invention when the tomograms are calculated in slices from radiator-proximate to radiator-distal.

Since the distance of the line detector from the radiator is known, the distortions can be computationally corrected. The images can be reproduced as undistorted tomograms or three-dimensional images or can be computationally combined again to form the standard, undistorted aggregate absorption image and can be reproduced.

This solution is advantageous because a separate ceph structure with boom is not thereby used.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostics installation for producing x-ray exposures of a body part, having a length and width, of a patient, said x-ray diagnostics installation comprising:

a line detector camera and a radiation source disposed diametrically opposite said line detector camera, and adapted to have said body part disposed between said radiation source and said line detector camera, said radiation source having a radiation diaphragm and emitting a fan beam of x-rays limited by said radiation diaphragm;

said line detector camera having a slot shaped opening for admitting x-rays from said radiation source, and containing an x-ray detector disposed behind said slot-shaped opening, said x-ray detector having a width matched to at least one of the width and the length of said body part;

means for producing a panorama tomogram of said body part of said patient;

means for producing a skull exposure of said patient; and adjustment means, to which said radiation source and said line detector camera are mounted, for adjusting said line detector camera relative to said body part for moving said slot opening along said body part and for moving said fan beam from said radiation source synchronously with said line detector camera, said adjustment means including a stand having a height-adjustable carrier part, a rotary unit mounted on said stand carrying said radiation source and a first means for positioning and holding the head of said patient, a boom carrying a second means for holding and positioning said head, first and second holders for said line detector camera, said first and second holders being structurally identical, said first holder being disposed on said rotary unit, relative to said first means for holding and positioning said head, for orienting said line detector camera with said slot-shaped opening vertically oriented from moving said line detector camera around said head in common with said radiation source to produce said panorama tomogram, and said second holder being disposed for holding said line detector camera with said slot-shaped opening horizontally oriented for moving the line detector camera in a vertical plane relative to said radiation source to produce said skull exposure.

2. An x-ray diagnostics installation as claimed in claim 1 wherein said x-ray detector comprises a CCD sensor and a scintillation layer preceding said CCD sensor.

3. An x-ray diagnostics installation as claimed in claim 2 wherein said CCD sensor contains fiber optics.

4. An x-ray diagnostics installation as claimed in claim 1 wherein said x-ray detector comprises an amorphous silicon sensor matrix covered by a scintillation layer.

5. An x-ray diagnostics installation as claimed in claim 1 wherein said means for producing a skull exposure comprises means for moving said line detector camera and said radiation source in a vertical direction.

6. An x-ray diagnostics installation as claimed in claim 1 further comprising means for compensating for motion of said height-adjustable carrier part during said skull exposure connected between said boom and said second means for positioning and holding said head.

7. An x-ray diagnostics installation as claimed in claim 1 wherein said line detector camera includes means for releasably mechanically and electrically connecting said line detector camera to each of said first and second holders.

8. An x-ray diagnostics installation as claimed in claim 1 wherein said means for producing a panorama tomogram moving said radiation source and said line detector camera in a horizontal direction.

9. An x-ray diagnostics installation as claimed in claim 1 further comprising a pre-diaphragm disposed in front of said line detector camera, and wherein said adjustment means comprises means for holding said line detector camera with said slot-shaped opening oriented horizontally and for executing an adjustment motion of said radiation diaphragm, said pre-diaphragm and said line detector camera in a vertical direction in common with a single drive, said radiation source remaining stationary during said adjustment motion.

10. A dental x-ray diagnostics installation for producing tomosynthetic exposures of an examination subject comprising:

a panorama exposure system including an x-ray radiator, an electronic line detector camera disposed opposite said x-ray radiator and adapted to receive an examination subject therebetween for producing a radiation image of said examination subject in said electronic line detector camera; and means for adjusting the position of said x-ray radiator in height relative to said subject and for pivoting said x-ray radiator around a vertical axis and around a horizontal axis for irradiating a point in said subject with x-rays from said x-ray radiator from a plurality of projection directions in respectively different planes.

11. An x-ray diagnostics installation as claimed in claim 10 wherein said means for adjusting comprises means for adjusting said x-ray radiator around said horizontal axis for setting a projection direction.

12. An x-ray diagnostics installation as claimed in claim 11 wherein said panorama exposure system includes a subject-proximate pre-diaphragm, and wherein said means for adjusting comprises means for simultaneously adjusting said x-ray radiator, said pre-diaphragm and said line detector camera.

13. An x-ray diagnostics installation as claimed in claim 10 wherein said means for adjusting comprises means for pivoting said x-ray radiator along a predetermined circular path around a radiator-distal, first vertical axis and for rotating said x-ray radiator in an opposite direction in a circular path around a radiator-proximate, second vertical axis.

14. An x-ray diagnostics installation as claimed in claim 10 further comprising a holder adapted to hold said subject between said x-ray radiator and said line detector camera, and wherein said means for adjusting is tiltably and pivotably mechanically connected to said holder for setting said projection directions.

15. An x-ray diagnostics installation as claimed in claim 10 wherein said means for adjusting comprises a live ring on which said x-ray radiator and said line detector camera are mounted diametrically opposite each other, and further comprising means for mounting said line detector camera on said live ring for rotation around a first, central vertical axis and for rotation around a second vertical axis, and further comprising means for mounting said x-ray radiator on said live ring for rotation around a third vertical axis.

16. An x-ray diagnostics installation as claimed in claim 15 further comprising a carrier, on which said live ring is mounted, said carrier defining said horizontal axis for setting said projection directions.

17. An x-ray diagnostics installation as claimed in claim 10 wherein said line detector camera has a slot-shaped opening having at least one of a width and length matched to a part of said subject for which said image is to be obtained, and an x-ray detector disposed behind said slot-shaped opening, and said installation further comprising line detector camera adjustment means for adjusting the position of said line detector camera relative to said part of said subject for moving said slot-shaped opening along said part, and said installation further comprising a radiation diaphragm for defining a fan beam of x-rays from said x-ray source, and means for moving said radiation diaphragm synchronously with said line detector camera.

18. An x-ray diagnostics installation as claimed in claim 17 wherein said line detector camera adjustment means comprises means for orienting said line detector camera with said slot-shaped opening proceeding horizontally and for producing an adjustment motion of said line detector camera in a vertical direction.

19. An x-ray diagnostics installation as claimed in claim 18 wherein said line detector camera adjustment means includes a boom on which said line detector camera is mounted, and wherein said means for adjusting the position of said x-ray radiator includes a height-adjustable stand on which said x-ray radiator is mounted.

20. An x-ray diagnostics installation as claimed in claim 15 wherein said line detector camera adjustment means comprises means for orienting said line detector camera with said slot-shaped opening proceeding vertically and for producing an adjustment motion of said line detector camera in a horizontal direction.

21. An x-ray diagnostics installation as claimed in claim 20 wherein said x-ray radiator generates an x-ray beam, and said installation further comprising a primary diaphragm disposed for gating said x-ray beam, and wherein said means for adjusting the position of said x-ray source comprises a rotary unit, having a center and on which said x-ray radiator and said primary diaphragm are mounted, for radially adjusting said x-ray source relative to said center and for rotating said x-ray source around said center.

22. An x-ray diagnostics installation as claimed in claim 10 wherein said line detector camera is disclosed subject-proximate for producing remote x-ray images of said subject, and further comprising means for calculating tomosynthetic tomograms of said subject from prescribed distances between said x-ray radiator, said subject and said line detector camera and for electronically correcting any image distortion arising due to the distance relationship between said x-ray source, said subject and said line detector camera.

* * * * *